United States Patent [19]

Murphy et al.

[11] 4,222,840
[45] Sep. 16, 1980

[54] HEATED SOLID ELECTROLYTE OXYGEN SENSOR

[75] Inventors: Michael P. Murphy, Flint; George W. Hillebrand, Davison, both of Mich.

[73] Assignee: General Motors Corporation, Detroit, Mich.

[21] Appl. No.: 892,643

[22] Filed: Apr. 3, 1978

[51] Int. Cl.² .................................................. G01N 27/58
[52] U.S. Cl. ................................................... 204/195 S
[58] Field of Search ........................... 204/15, 195 S; 123/119 E

[56] References Cited

U.S. PATENT DOCUMENTS

| | | | |
|---|---|---|---|
| 3,546,086 | 12/1970 | Sayles | 204/195 S |
| 3,616,274 | 10/1971 | Eddy | 204/1 S |
| 3,815,560 | 6/1974 | Wahl et al. | 123/117 R |
| 3,844,920 | 10/1974 | Burgett et al. | 204/195 S |
| 3,915,828 | 10/1975 | Cleary et al. | 204/195 S |
| 3,928,161 | 12/1975 | McIntire et al. | 204/195 S |
| 3,999,947 | 12/1976 | Mihara et al. | 23/254 E |
| 4,040,930 | 8/1977 | Dillon | 204/195 S |
| 4,107,019 | 8/1978 | Takao et al. | 204/195 S |

FOREIGN PATENT DOCUMENTS 2131365  11/1972  France .
1367389  9/1974  United Kingdom .

*Primary Examiner*—G. L. Kaplan
*Attorney, Agent, or Firm*—Robert J. Wallace

[57] ABSTRACT

A readily manufacturable heated solid electrolyte oxygen sensor. The sensor includes a generally planar heater supported on a tubular reference electrode terminal in desired position normal to the longitudinal axis of said terminal and parallel to a generally planar solid electrolyte member within a cylindrical housing. The heater and terminal form a subassembly readily assemblable in concentric relationship with the planar solid electrolyte member and the cylindrical housing.

1 Claim, 3 Drawing Figures

HEATED SOLID ELECTROLYTE OXYGEN SENSOR

BACKGROUND OF THE INVENTION

This invention relates to a heated galvanic-type solid electrolyte oxygen sensor, and more particularly to an improved and readily assemblable construction of such a sensor in which the solid electrolyte member and the heater are generally planar.

Solid electrolyte galvanic oxygen sensors essentially include an oxygen-ion-conductive ceramic body with porous electrodes on opposite faces of the body. One electrode is exposed to a reference source of oxygen. The other electrode is exposed to a source whose oxygen content is to be measured. A difference in oxygen partial pressure at the electrodes results in a corresponding electrode potential difference, providing a sensor output voltage.

The output voltage of such sensors can be used to measure oxygen or unburned combustibles in combustion gases produced by an internal combustion engine. This voltage can be used in monitoring and controlling the combustion process, as disclosed in U.S. Pat. No. 4,129,099 Howarth, and U.S. Pat. No. 3,616,274 Eddy and U.S. Pat. No. 3,844,920 Burgett et al.

The solid electrolyte of such a sensor must be heated to an elevated temperature to obtain an appreciable output voltage. Also, sensor output voltage varies directly with changes in temperature, especially at lower operating temperatures. Combustion gases can be used to heat the sensor to operating temperatures but such gases vary widely in temperature, particularly when from an internal combustion engine. The aforementioned U.S. Pat. No. 3,616,724 Eddy discloses sensor temperature compensating means that includes a surrounding resistance heater. U.S. Pat. No. 3,815,560 Wahl et al. discloses a surrounding resistive heater to maintain an electrolyte tube at high temperatures where its output voltage is least affected by temperature change. The aforementioned U.S. Pat. No. 4,129,099 Howarth discloses doping the solid electrolyte with iron oxide for temperature compensation. It additionally discloses disposing a resistance heater inside a solid electrolyte tube for maintaining the sensor at higher operating temperatures and for supplemental heating on start up.

For automotive applications, the heated sensor should be particularly rugged and reliable. In addition, for higher reliability and lower cost, the heated sensor should be simple and readily manufacturable. U.S. Pat. application Ser. No. 892,644 now U.S. Pat. No. 4,175,019 entitled "Heated Solid Electrolyte Oxygen Sensor", concurrently filed herewith in the name of Michael P. Murphy, a co-inventor herein, discloses a new way to incorporate a heater in the oxygen sensor, particularly an automotive oxygen sensor. His invention involves forming a subassembly of the heater and the sensor reference electrode terminal. In the subassembly, the heater is prealigned so that when the reference electrode terminal is assembled with its solid electrolyte, the heater is also inherently aligned with the solid electrolyte. In summary, Murphy proposes adding a heater to a solid electrolyte oxygen sensor as a subassembly with a reference electrode terminal for the solid electrolyte. The heater-electrode terminal subassembly is particularly useful in an oxygen sensor such as disclosed in U.S. Pat. No. 3,844,920 Burgett et al.

FIGS. 9–11 of the drawing in the aforementioned U.S. Pat. application Ser. No. 892,644 now U.S. Pat. No. 4,175,019 disclose a specific construction in which a heater-electrode terminal subassembly is used with a solid electrolyte member that is a flat disc. This specific construction is not specifically claimed therein and is not suggested by the other embodiments disclosed therein. It is, therefore, considered to be an improvement on the invention claimed in the aforementioned U.S. Pat. application Ser. No. 892,644 now U.S. Pat. 4,175,019.

OBJECTS AND SUMMARY OF THE INVENTION

It is, therefore, an object of this invention to provide an improved heated solid electrolyte galvanic sensor.

These and other objects of the invention are attained in a solid electrolyte galvanic oxygen sensor having a planar-type heater supported on and normal to a tubular reference electrode terminal in a desired predetermined spaced relationship with respect to a planar solid electrolyte member. The heater and terminal comprise a subassembly readily assemblable with the planar electrolyte member and a surrounding metal housing. Means coacting with terminal and housing flanges hold the electrolyte member, heater-terminal subassembly and housing in a fixed predetermined relationship.

BRIEF DESCRIPTION OF THE DRAWINGS

Other objects, features and advantages of the invention will become more apparent from the following description of the preferred embodiment thereof and from the drawings, in which.

DESCRIPTION OF THE PREFERRED EMBODIMENTS

Figure 1:
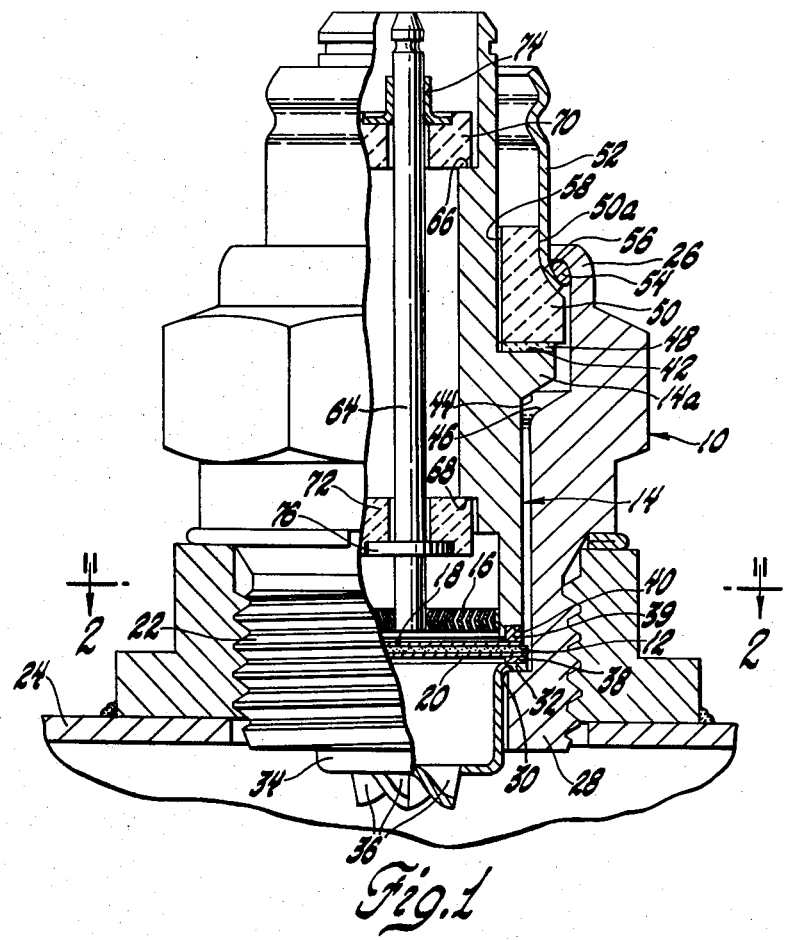
FIG. 1 is an elevational view in partial section showing an oxygen sensor made in accordance with the invention.
Figure 3:
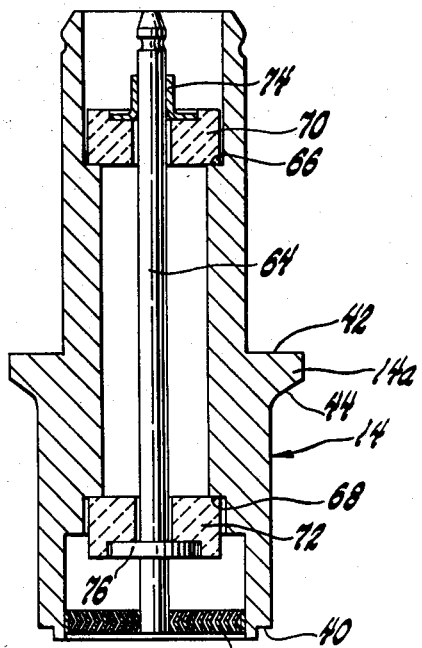
FIG. 3 is a sectional view showing the heater-electrode terminal subassembly in the sensor shown in FIGS. 1 and 2.
Figure 2:
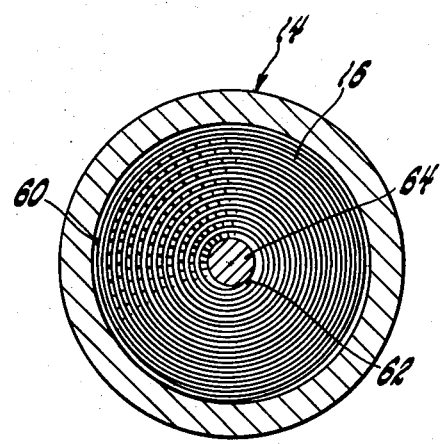
FIG. 2 is a sectional view along the line 2—2 of FIG. 1.

Reference is now made to the drawing hereof, which in FIGS. 1–3 shows a tubular metal shell 10, a circular flat disc 12 of solid electrolyte material, a tubular electrode terminal 14, and an electrical resistance heating element 16. Electrode terminal 14 has an outward circumferential flange 14a. Porous platinum electrodes 18 and 20 cover the upper and lower parallel surfaces of electrolyte disc 12.

Shell 10 has external threads 22 by which it is secured within a threaded aperture in an automobile exhaust pipe 24. In some instances, it may be preferred to alternatively place the sensor in an automobile exhaust manifold or tailpipe, or in a passage parallel thereto. Shell 10 also has an inward upper circumferential flange 26 and an inward lower circumferential flange 28 for clamping sensor components together in a coaxial relationship. Upper flange 26 is formed by rolling or crimping after nesting sensor components within a shell 10. Lower flange 28 forms a circumferential shoulder 30 that is normal to the longitudinal axis of shell 10.

Disposed on lower shoulder 30 is an outward circumferential flange 32 on a generally cup-shaped lower metal shield 34. Shield 34 has louvers 36 in its bottom end to permit exhaust gases to enter the shield and contact the lower platinum electrode 20. An annular soft metal sealing ring 38 is congruently disposed on flange 32. Circular electrolyte disc 12 has a diameter about 0.005–0.01 inch less than the radially adjacent inner diameter of shell 10. Electrolyte disc 12 is coaxially seated on sealing ring 38, with its lower platinum electrode 20 contacting sealing ring 38. Accordingly, shell 10 is in low resistance electrical communication with disc lower electrode 20.

A second soft metal sealing ring 39 is coaxially disposed on the upper surface of electrolyte disc 12 and contacts the upper platinum electrode 18. To insure electrical separation, upper platinum electrode 18 does not completely extend to the edge of electrolyte disc 12. It only extends far enough across the upper face of disc 12 to make electrical contact with upper soft metal sealing ring 39. Upper sealing ring 39 nests within a recess 40 in the lower end face of electrode terminal 14. Thus, electrode terminal 14 is in low resistance electrical communication with disc upper electrode 18. The end face of electrode terminal 14 is normal to the longitudinal axis of terminal 14. Thus, it is parallel to shoulder 30 on shell 10.

Flange 14a extends around the entire circumference of electrode terminal 14 about midway along the electrode terminal length. The upper surface 42 of flange 14a is normal to the longitudinal axis of electrode terminal 14. The lower surface 44 of flange 14a is uniformly spaced from an adjacent inner circumferential shoulder 46 on shell 10. Successively disposed on terminal flange upper surface 42 is a flat mica washer 48, a ceramic ring 50, a tubular upper metal shield 52 and an annular soft steel gasket 54. Ceramic ring 50 has an upward, decreasing, taper 50a on its outer surface. The lower end 56 of upper shield 52 is flared to conform to the ceramic ring taper 50a and rests on the tapered outer surface of ceramic ring 50. It is clamped against the tapered outer surface 50a of the ceramic ring 50 by the upper shell flange 26 through the soft steel ring 54. All of the aforementioned components are coaxially aligned. Further, upper metal shield 52 is in low resistance electrical communication with shell 10, and lower platinum electrode 20.

The solid electrolyte disc 12 can be of any suitable oxygen-ion-conductive ceramic, as for example stabilized zirconia, thoria, or the like. Cubic zirconia stabilized with 8 mole percent yttria or 15 mole percent calcia can be used. The electrodes 18 and 20 and solid electrolyte disc 12 are preferably catalytic, particularly electrode 20. For a catalytic electrode, platinum is preferred. It can be formed in the usual manner, as by brushing or spraying of a platinum paste onto the the disc 12 and subsequently firing it. On the other hand, electrodes 18 and 20 could be formed by evaporation or sputtering.

The sealing rings 38 and 39 can be of any soft metal, such as copper or nickel. The shell 10, electrode terminal 14, metal shield 34 and 52, and metal components within electrode terminal 14 are made of metal which will withstand the conditions of sensor use, as for example at least stainless steel and preferably a nickel-based alloy. Ceramic ring 50 can be of any suitable electrically insulating material, as for example alumina.

Ceramic ring 50 has an inner cylindrical surface 58 of a diameter only slightly larger than the outer diameter of electrode terminal 14 above terminal flange 14a. A spacing of only about 0.040 or less can be used. Inner cylidndrical surface 58 on ceramic ring 50 is specifically concentric with the tapered surface 50a on the outer periphery of ceramic ring 50. The side surfaces on ceramic ring 50 are thus not only mutually coaxial but coaxial with shell 10, disc 12 and electrode terminal 14. This coacts with the close fitting relationship between ceramic ring 50 and electrode terminal 14 to maintain electrode terminal 14 coaxial with shell 10 when clamped between shell flanges 26 and 28. Accordingly, electrode terminal 14 does not contact shell 10. They remain mutually electrically isolated. Terminal 14 has an outer diameter at least about 0.01 inch less than the radially adjacent inner diameter of shell 10, to insure the electrical isolation. However, if desired, an insulating sleeve (not shown) can be included in the assembly around terminal 14 within shell 10, below terminal flange 14a. If the insulating sleeve has a wall thickness only slightly less than the space between the electrode terminal and shell 10, it can help maintain the terminal and shell electrically isolated and coaxial.

As more clearly seen in FIG. 3, the resistive heating element 16 and electrode terminal 14 are part of a preformed subassembly. Resistance heating element 16 is a planar coil, or spiral, such as a heating element for an automobile cigar lighter. It presents an effectively flat heating face. The outer end of the spiral of coil 16 is welded at 60 to the lower end of electrode terminal 14. The inner end of the spiral of coil 16 is welded at 62 to the lower end of a coaxial heater terminal 64. Electrode terminal 14 thus forms a common terminal for both the heater coil 16 and reference electrode 18 on disc 12. Heating coil 16 forms a generally planar heater having an effectively flat heating face that is normal to the longitudinal axis of electrode terminal 14 having an effectively flat heating face that is normal to the longitudinal axis of electrode terminal 14. Since shell 10 is coaxial with electrode terminal 14, heating coil 16 is also normal to the longitudinal axis of shell 10. Accordingly, the heating face of coil 16 is parallel to the upper surface of disc 12.

Heater terminal 14 is coaxially disposed within electrode terminal 64. It is affixed within electrode terminal 14 by oppositely facing shoulders 66 and 68 on the interior of electrode terminal 14. Shoulders 66 and 68 respectively engage upper insulating ring 70 and lower insulating ring 72. Insulating rings 70 and 72 coaxially align heater terminal within electrode terminal 14. Insulating rings 70 and 72 are respectively clamped against shoulders 66 and 68 by a flanged spring clip 74 on the upper end of heater terminal 64 and a circumferential flange 76 on the lower end of heater terminal 64. If desired, the upper ends of electrode terminal 14, upper shield 52 and heater terminal 64 can be silver plated (not shown) to enhance low resistance terminal connections.

The embodiments of the invention in which an exclusive property or privilege is claimed are defined as follows:

1. In a galvanic exhaust gas sensor having a circular solid electrolyte member, a heater in subassembly with an outwardly flanged concentric tubular terminal for a reference electrode on said electrolyte member, an inwardly flanged concentric tubular metal shell surrounding said member and said heater-terminal subassembly, and means coacting with said terminal and shell flanges for holding said member, heater-terminal subassembly and shell together in a fixed predetermined concentric relationship, the improvement wherein said solid electrolyte member is a substantially flat circular disc having a reference electrode on one face, said heater includes a spiral resistance heating element having a substantially flat heating face, and said subassembly includes an elongated heating element terminal coaxially extending through said tubular electrode terminal, and electrical insulating means for supporting said heating element terminal on said electrode terminal in a fixed placement along the longitudial axis of said electrode terminal, each of said terminals having one end adjacent one end on the other terminal, said adjacent ends on said terminals respectively affixed to opposite ends of said heating element spiral with said flat heating face normal to said longitudinal axis, whereby coaxial assembly of said electrolyte disc, heater-terminal subassembly, and shell inherently aligns said disc and element faces and generally parallelly spaces them a fixed predetermined distance apart.

* * * * *